US010213514B2

(12) United States Patent
Bovin et al.

(10) Patent No.: US 10,213,514 B2
(45) Date of Patent: Feb. 26, 2019

(54) FUNCTIONALIZING NANOFIBRES

(71) Applicants: Nicolai Bovin, Moscow (RU); Stephen Henry, Auckland (NZ); Iain Hosie, Auckland (NZ); Stephen Parker, Auckland (NZ)

(72) Inventors: Nicolai Bovin, Moscow (RU); Stephen Henry, Auckland (NZ); Iain Hosie, Auckland (NZ); Stephen Parker, Auckland (NZ)

( * ) Notice: Subject to any disclaimer, the term of this patent is extended or adjusted under 35 U.S.C. 154(b) by 0 days.

(21) Appl. No.: 15/598,505

(22) Filed: May 18, 2017

(65) Prior Publication Data

US 2017/0252460 A1 Sep. 7, 2017

Related U.S. Application Data

(63) Continuation of application No. 15/101,007, filed as application No. PCT/NZ2014/050015 on Dec. 2, 2014, now Pat. No. 9,814,786.

(30) Foreign Application Priority Data

Dec. 2, 2013 (NZ) ........................ 618502
Dec. 2, 2013 (NZ) ........................ 618508

(51) Int. Cl.
| *A61K 47/69* | (2017.01) |
| *C07F 9/655* | (2006.01) |
| *C07F 9/6558* | (2006.01) |
| *C07F 9/6561* | (2006.01) |
| *A61K 49/00* | (2006.01) |
| *A61K 31/7028* | (2006.01) |
| *A61L 27/16* | (2006.01) |
| *A61L 27/20* | (2006.01) |
| *A61L 27/54* | (2006.01) |
| *A61L 15/26* | (2006.01) |
| *A61L 15/28* | (2006.01) |
| *A61L 15/44* | (2006.01) |
| *D01D 5/00* | (2006.01) |
| *D01F 1/10* | (2006.01) |
| *A61L 27/18* | (2006.01) |
| *A61K 47/54* | (2017.01) |
| *A61K 47/55* | (2017.01) |
| *A61K 47/59* | (2017.01) |
| *A61K 47/61* | (2017.01) |
| *A61K 47/64* | (2017.01) |

(52) U.S. Cl.
CPC ...... *A61K 47/6953* (2017.08); *A61K 31/7028* (2013.01); *A61K 47/543* (2017.08); *A61K 47/544* (2017.08); *A61K 47/551* (2017.08); *A61K 47/59* (2017.08); *A61K 47/595* (2017.08); *A61K 47/61* (2017.08); *A61K 47/6435* (2017.08); *A61K 49/0043* (2013.01); *A61K 49/0054* (2013.01); *A61K 49/0093* (2013.01); *A61L 15/26* (2013.01); *A61L 15/28* (2013.01); *A61L 15/44* (2013.01); *A61L 27/16* (2013.01); *A61L 27/18* (2013.01); *A61L 27/20* (2013.01); *A61L 27/54* (2013.01); *C07F 9/6561* (2013.01); *C07F 9/65522* (2013.01); *C07F 9/65586* (2013.01); *D01D 5/003* (2013.01); *D01D 5/0069* (2013.01); *D01F 1/10* (2013.01); *A61L 2300/22* (2013.01); *A61L 2300/60* (2013.01); *A61L 2400/14* (2013.01); *A61L 2430/00* (2013.01)

(58) Field of Classification Search
CPC ........ A61K 47/48976; A61K 47/48192; A61K 47/4823; A61K 47/48207; A61K 47/48292; A61K 47/48107; A61K 47/48053; A61K 47/48046; A61K 49/0093; A61K 49/0054; A61K 49/0043; A61K 31/7028; D01F 1/10; D01D 5/0069; D01D 5/003; A61L 27/16; A61L 27/54; A61L 27/18; A61L 27/20; A61L 15/44; A61L 15/28; A61L 15/26; A61L 2430/00; A61L 2300/22; A61L 2300/60; A61L 2400/14; C07F 9/6561; C07F 9/65586; C07F 9/65522
See application file for complete search history.

(56) References Cited

U.S. PATENT DOCUMENTS

| 2006/0240110 | A1 | 10/2006 | Kiick et al. | |
| 2006/0260707 | A1* | 11/2006 | Frey | ........................ D04H 3/02 138/140 |
| 2007/0274862 | A1* | 11/2007 | Harttig | ................. G01N 33/543 422/400 |
| 2012/0184461 | A1* | 7/2012 | Bovin | ................ G01N 33/5308 506/13 |

(Continued)

FOREIGN PATENT DOCUMENTS

| WO | WO 2005/090368 A1 | 9/2005 |
| WO | WO 2008/030115 A2 | 3/2008 |

(Continued)

OTHER PUBLICATIONS

Huang, Xiao-Jun, et al; "Electrospun Nanofibers Modified with Phospholipid Moieties for Enzyme Immobilization"; *Macromolecular Rapid Communications*; vol. 27, pp. 1341-1345 (2006).

(Continued)

*Primary Examiner* — Robert S Jones
(74) *Attorney, Agent, or Firm* — Nixon & Vanderhye P.C.

(57) ABSTRACT

Methods for functionalizing the surface of nanofiber substrates, including electrospun fibers and non-woven or woven mats of fibers are described. Functionalized nanofiber substrates presenting biologically active moieties such as biotin and saccharides are described.

5 Claims, 11 Drawing Sheets

(56) References Cited

U.S. PATENT DOCUMENTS

2013/0125912 A1    5/2013  Tojo et al.

FOREIGN PATENT DOCUMENTS

| WO | WO 2009/048343 A1 | 4/2009 |
| WO | WO 2009/133059 A2 | 11/2009 |
| WO | WO 2011/002310 A1 | 1/2011 |
| WO | WO 2013/035072 A1 | 3/2013 |
| WO | WO 2013/144206 A1 | 10/2013 |

OTHER PUBLICATIONS

Supaphol, Pitt, et al; "Electrospinning of Biocompatible Polymers and Their Potentials in Biomedical Applications"; *Adv. Polym. Sci.*; vol. 246, pp. 213-240 (2012).

Yoo, Hyuk Sang, et al; "Surface-Functionalized Electrospun Nanofibers for Tissue Engineering and Drug Delivery"; *Advanced Drug Delivery Reviews*; vol. 61, pp. 1033-1042 (2009).

\* cited by examiner

FUNCTIONALIZING NANOFIBRES

This application is a continuation of Application No. 15/101,077, filed Jun. 2, 2016 which is a 371 of PCT/NZ2014/050015, filed Dec. 2, 2014, which claims priority to New Zealand Patent Application Nos. 618502 filed Dec. 2, 2013, and 618508 filed Dec. 2, 2013, the entire contents of each of which are hereby incorporated by reference.

FIELD OF INVENTION

The invention relates to a method of functionalising the surface of nanofibre substrates. The substrates may take the form of either individual fibres or mats of non-woven or woven fibres. In particular, the invention relates to electrospun nanofibre substrates functionalised to present biologically active moieties at their surface.

BACKGROUND ART

Functionalized nanofibres and matrices have potential in numerous biomedical applications including tissue engineering, wound dressing, drug delivery and enzyme immobilization. Electrospinning is a method commonly used in the preparation of such nanofibres and matrices.

The publication of Kiick et al (2006) discloses functionalized electrospun matrices. In addition to the matrix polymer, the matrices comprise a compatibilizing polymer and a biomolecule or other small, functioning molecule. The biomolecule or other small functioning molecule is conjugated to an intermediate molecular weight polymer; the "compatibilizing polymer". This attachment is stated to provide effective retention over time scales relevant for biological and other potential applications.

The publication of Seiler et al (2009) discloses a nanofibre matrix comprising an active agent suspended or enmeshed in electrospun hyperbranched polymers. The use of the matrices in cosmetics, drug delivery and for the growth of cells is suggested.

Bovin et al (2011) discloses the localisation of a functional moiety to the surface of a substrate by inkjet printing of an aqueous dispersion of a lipid conjugate of the functional moiety.

The publication of Supaphol et al (2012) has reviewed the electrospinning of biocompatible polymers and their potential in biomedical applications such as tissue engineering, wound dressings, drug delivery and enzyme immobilization. Naturally derived and synthetic polymers (including block polymers and copolymers) that may be electrospun to produce nanofibres include cellulose acetate (CA), collagen, chitin, chitosan, gelatin, fibrinogen, nylon (PA6/PA66), poly(acrylonitrile-co-acrylic acid) (PANCAA), polyacrylonitrile-co-2-hydroxyethyl methylacrylate) (PANCHEMA), poly($\epsilon$-caprolactone) (PCL), poly(p-dioxane-co-L-lactide)-block-poly ethylene glycol) (PPDO/PLLA-b-PEG), poly(ethylene glycol) (PEG), poly(ethylene oxide) (PEO), poly(ethylene-co-vinyl acetate) (PEVA, poly(lactic acid) (PLA), poly(DL-lactide acid) (PDLLA), poly(L-lactic acid) (PLLA), poly(lactic-co-glycolic acid) (PLGA), poly(vinyl acetate) (PVA), poly(vinyl alcohol) (PVOH), poly[(2-propyl-1,3-dioxane-4,6-diyl)methylene] (polyvinyl butyrol; PVB), poly(N-vinyl-2-pyrrolidone) (PVP) and zein. Blends of these polymers may be selected to optimise production of nanofibres.

The publication of Tojo et al (2013) discloses a nanofibre electrospun from, a water soluble polymer having cavities containing an oily component. Again, the composition is suggested for use in cosmetics.

The publication of Vile et al (2013) also discloses nanofibres comprising active ingredients. The nanofibres are formed by mixing the active ingredients and polymers in a solvent phase before electrospinning. A wide variety of active ingredients are suggested for inclusion in the nanofibres. Matrices and bioactive dressings or patches for use in wound healing and skin repair are disclosed.

The publication of Garcia et al (2013) discloses nonwoven membranes comprising electrospun nanofibres and microparticles of cosmetic or therapeutic active agents entangled between the nanofibres.

It is an object of the present invention to provide facile methods of functionalizing the surface of nanofibre substrates or at least to provide the public with a useful choice.

STATEMENT OF INVENTION

In a first aspect the invention provides a functionalized nanofibre comprising an electrospun polymer and a water soluble synthetic construct of the structure F-S-L where F is a functional moiety, L is a lipid and S is a spacer linking F to L via covalent bonds.

In a second aspect the invention provides a method of preparing a functionalized electrospun nanofibre comprising the step of:
1. Preparing a dispersion of a polymer and a water soluble synthetic construct of the structure F-S-L in admixture in a liquid medium; and then
2. electrospinning the polymer from the liquid medium to provide the functionalized nanofibre, where F is the functional moiety, L is a lipid and S is a spacer linking F to L via covalent bonds.

In a third aspect the invention provides a method of localising a functional moiety to at least one discrete area on a surface of a nanofibre substrate comprising the step of propelling droplets of an aqueous dispersion of a water soluble synthetic construct of the structure F-S-L from a plurality of orifices located in a monolithic print head onto the surface of the nanofibre substrate, where F is the functional moiety, L is a diacyl- or dialkyl lipid and S is a spacer linking F to L via covalent bonds. Preferably, the nanofibres of the nanofibre substrata are electrospun nanofibres.

The following preferments apply to each of the aspects of the invention.

Preferably, the polymer is selected from the group consisting of: cellulose acetate (CA), collagen, chitin, chitosan, gelatin, fibrinogen, nylon (PA6/PA66), poly(acrylonitrile-co-acrylic acid) (PANCAA), poly(acrylonitrile-co-2-hydroxyethyl methylacrylate) (PANCHEMA), poly($\epsilon$-caprolactone) (PCL), poly(p-dioxane-co-L-lactide)-block-poly (ethylene glycol) (PPDO/PLLA-b-PEG), poly(ethylene glycol) (PEG), poly(ethylene oxide) (PEO), poly(ethylene-co-vinyl acetate) (PEVA, poly(lactic acid) (PLA), poly(DL-lactide acid) (PDLLA), poly(L-lactic acid) (PLLA), poly(lactic-co-glycolic acid) (PLGA), poly(vinyl acetate) (PVA), poly(vinyl alcohol) (PVOH), poly[(2-propyl-1,3-dioxane-4,6-diyl)methylene] (polyvinyl butyrol; PVB), poly(N-vinyl-2-pyrrolidone) (PVP), zein and blends thereof. More preferably, the polymer is dispersible in alcohol or water. Most preferably, the polymer is cellulose acetate (CA) or poly[(2-propyl-1,3-dioxane-4,6-diyl)methylene] (PVB).

Preferably, the diameter of greater than 95% of the eiectrospun nanofibre is in the range 10 to 1000 nm. More preferably, the diameter of greater than 95% of the electrospun nanofibre is in the range 10 to 500 nm.

Preferably, F is a functional moiety selected from the group consisting of: biotin, mono-, di-, tri- or oligosaccharides, oligopeptides and fluorophores of fluorescein. More preferably, F is a functional moiety selected from the group consisting of: biotin, mono-, di-, tri- or oligosaccharides, oligopeptides and fluorophores of fluorescein.

Preferably, L is a diacyl- or dialkyl-glycerolipid. More preferably, L is a diacyl- or dialkyl-glycerophospholipid. Yet more preferably, L is a diacylglycerophospholipid. Yet even more preferably, L is a phosphatidylethanolamine. Most preferably, L is dioleoylphosphatidylethanolamine (DOPE).

Preferably, S is selected from the group consisting of:

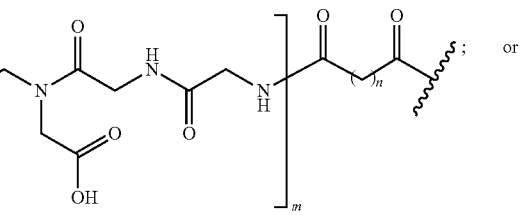

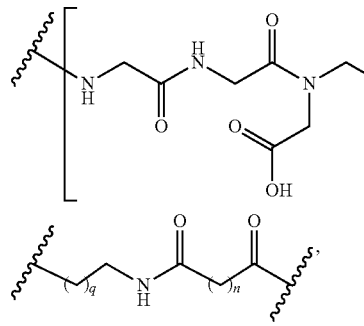

where m is the integer 1, 2 or 4, n is the integer 3, 4 or 5, p is the integer 1, 2 or 3 and q is the integer 2, 3, 4, 5 or 6.

In the description and claims of this specification the following abbreviations, acronyms, terms and phrases have the meaning provided: "comprising" means "including", "containing" or "characterized by" and does not exclude any additional element, ingredient or step; "consisting of" means excluding any element, ingredient or step not specified except for impurities and other incidentals; "consisting essentially of" means excluding any element, ingredient or step that is a material limitation; "dispersion" means a uniform dispersal of components in a medium and includes colloids and solutions; "fluorophores of fluorescein" means the fluorophores of fluorescein and its congeners (including eosin, Alexa Fluor 488™, Oregon Green™, Pennsylvania Green™, Tokyo Green™ and tetramethylrhodamine); "Functionalized nanofibres" means a nanofibre having functional moieties expressed or presented at its surface; "localised" means associated with a surface by non-covalent interactions and "localising" and "localisation" have a corresponding meaning; "polymer blend" means a homogenous or heterogeneous physical mixture of two or more polymers; "synthetic" means prepared by chemical synthesis; "water soluble" means, in the context of describing the properties of constructs of the general structure F-S-L (where F is a functional moiety, S is a spacer and L is a lipid), a stable, single phase system is formed at a temperature of 25° C. when the construct is contacted with water at a concentration of at least 100 μg/mL and in the absence of organic solvents or detergents.

The terms "first", "second", "third", etc. used with reference to elements, features or integers of the subject matter defined in the Statement of Invention and Claims, or when used with reference to alternative embodiments of the invention are not intended to imply an order of preference. Where concentrations or ratios of reagents are specified the concentration or ratio specified is the initial concentration or ratio of the reagents. Where values are expressed to one or more decimal places standard rounding applies. For example, 1.7 encompasses the range 1.6500 recurring to 1.7499 recurring.

The invention will now be described with reference to embodiments or examples and the figures of the accompanying drawings pages.

DETAILED DESCRIPTION

The biologically active moieties are introduced in the form of water dispersible lipid conjugates (constructs) of the generic structure F-S-L where F is the functional moiety, L is the lipid and S is a spacer covalently linking F to L. Without wishing to be bound by theory it is believed that the amphipathic nature of the constructs favours expression of the functional moiety at the surface whether the moiety is introduced at the time the fibres are electrospun or following formation of a mat of electrospun fibres. In the latter circumstance the constructs may be printed onto the surface of the mat of electrospun fibres in the form of an aqueous dispersion using conventional ink jet printing techniques. Higher resolution is achievable when the constructs are printed onto a nanofibre substrate, such as a mat of electrospun fibres. In either case, the functionalization of the surface of the electrospun nanofibres is achieved with greater efficiency then would be achieved by preparing a dispersion of polymer and functional moiety alone.

Constructs of the structure F-S-L that may be added to dispersions of these polymers include the constructs designated KODE™-fluorescein (I), KODE™-biotin (II) and KODE™-A$_{tri}$ (III):

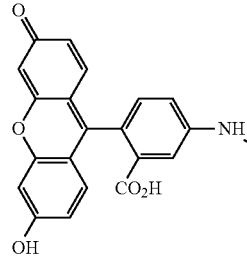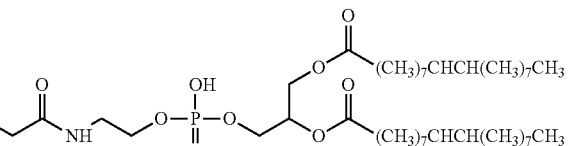

I (where F is fluorescein thiocyanate);

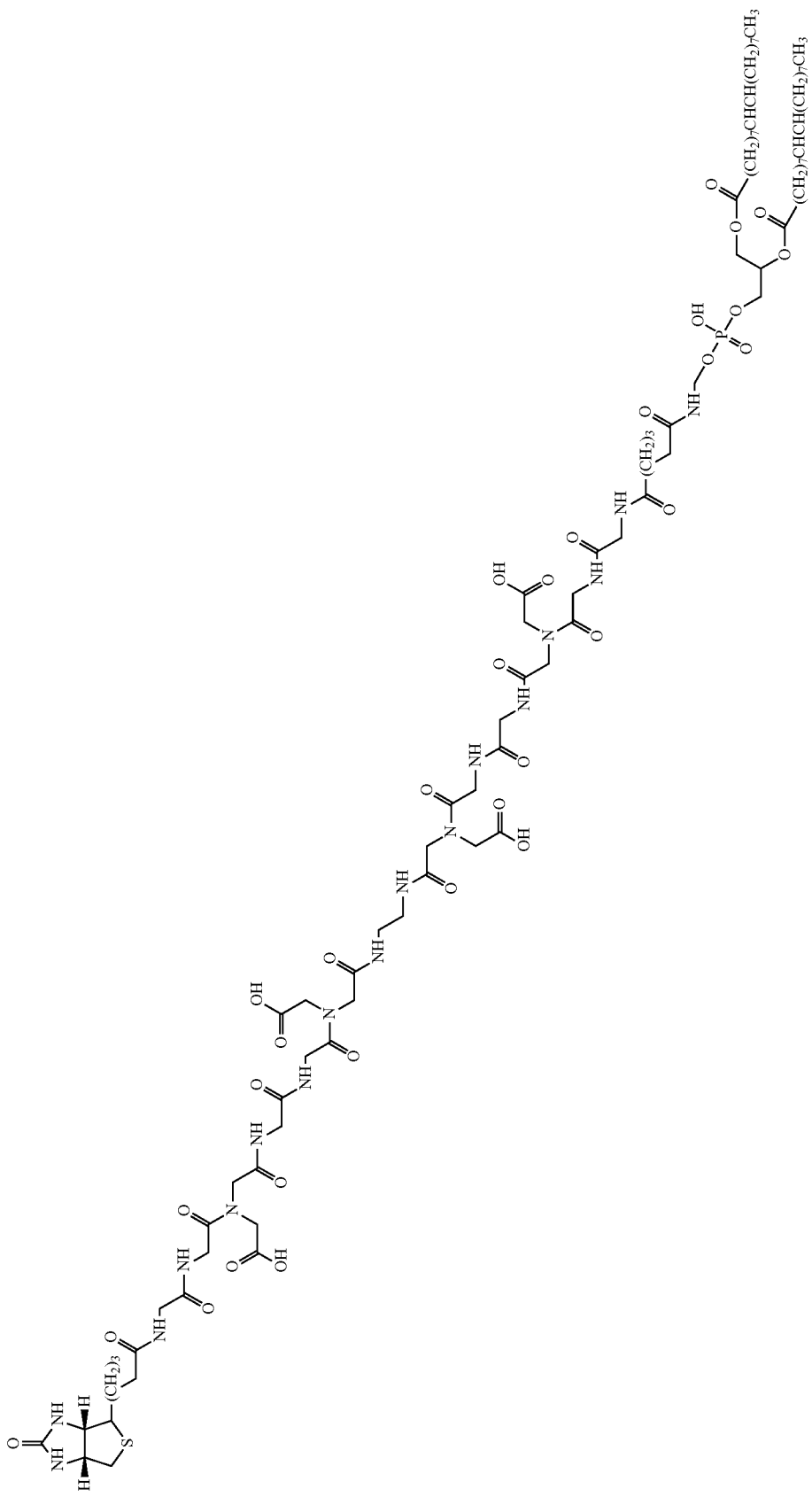

II (where F is biotin); and

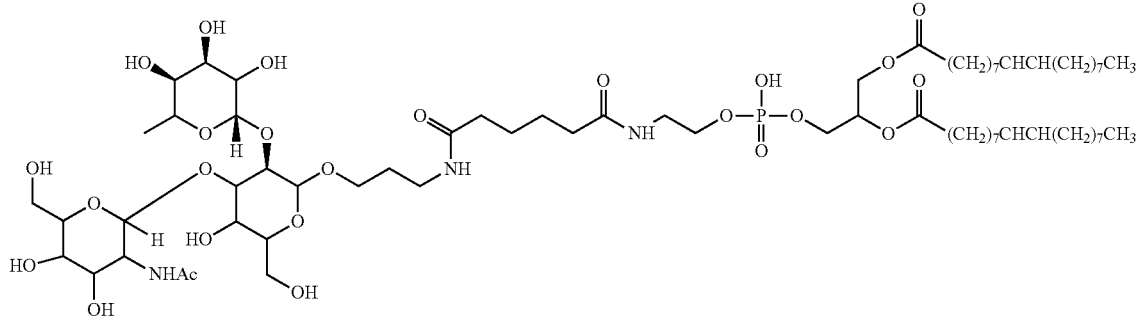

III (where F is $A_{tri}$).

The preparation of the construct designated KODE™-fluorescein (I) is described in the publication of Korchagina et al (2008). The preparation of the construct designated KODE™-biotin (II) is described in the publication of Bevin et al (2009). The preparation of the construct designated KODE™-$A_{tri}$ (III) is described in the publication of Bovin et al (2005).

EXPERIMENTAL

Preparation of Electrospun Nanofibres

Figure 1:
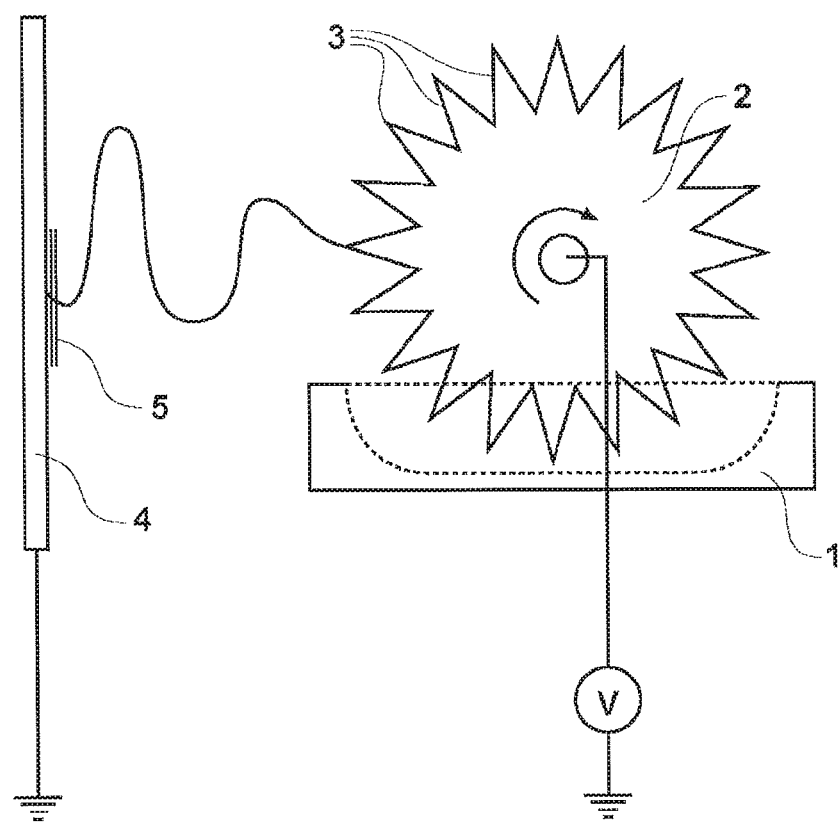
FIG. 1. A schematic representation of the apparatus used to prepare the electrospun nanofibres.
Figure 2:
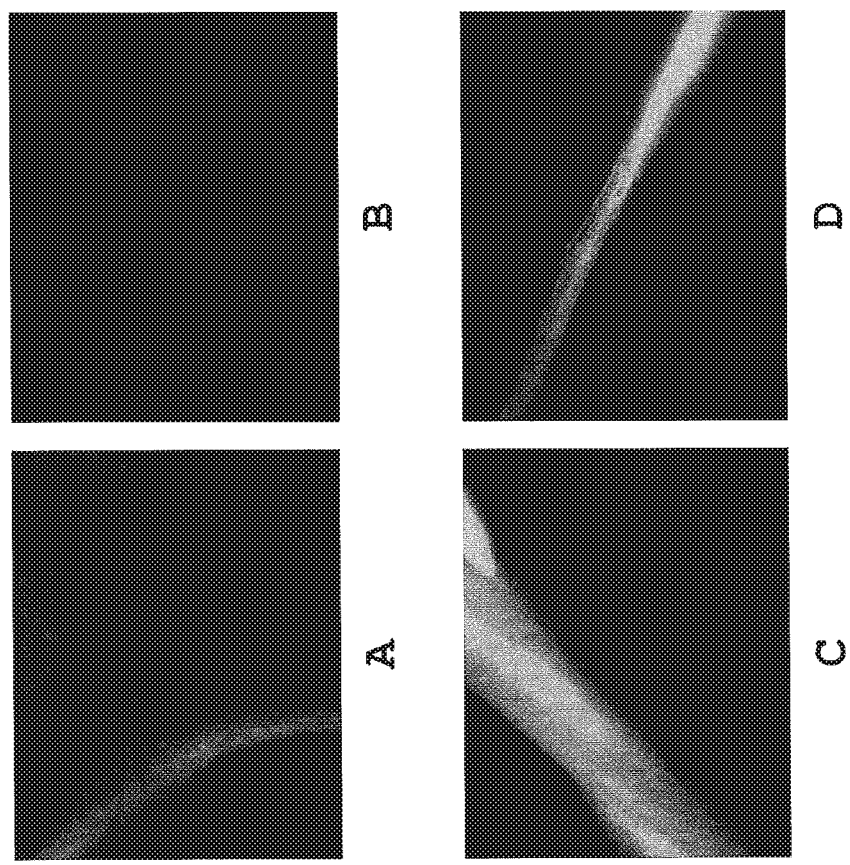
FIG. 2. Photomicrographs of nanofibres electrospun from a dispersion of PVB and the construct designated KODE™-fluorescein (I) before (A and B) and after (B and D) washing with methanol tipper photomicrographs (A and B) are at higher magnification.
Figure 3:
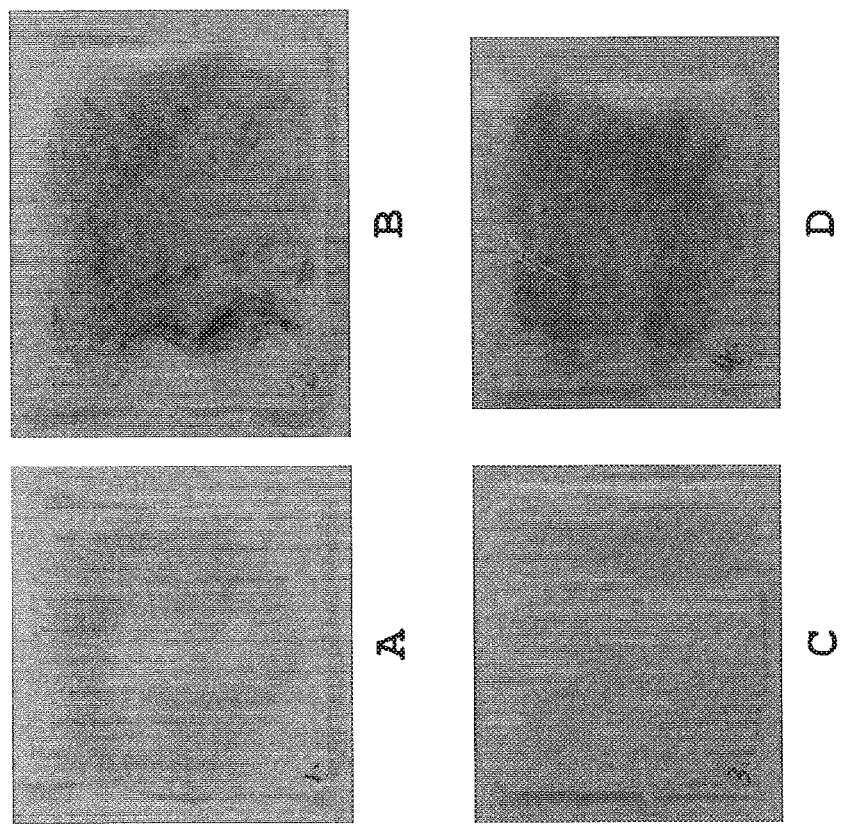
FIG. 3. Photographs of immunostained samples of mats of nanofibres electrospun from dispersions of PVB alone (A), PVB in admixture with the construct designated KODE™-biotin (II), PVB in admixture with biotin par se (C), and PVB in admixture with the construct designated KODE™-biotin (II) after washing with methanol prior to immunostaining (D).
Figure 4:
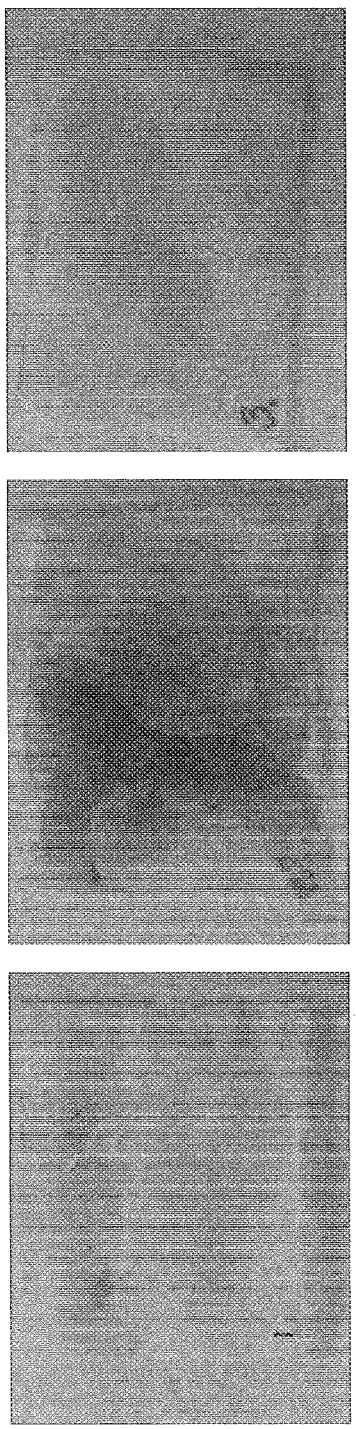
FIG. 4. Photographs of immunostained samples of mats of nanofibres electrospun from dispersions of PVB alone (A), PVB in admixture with the construct designated KODE™-$A_{tri}$ (III) (B), and PVB in admixture with the construct designated KODE™-$A_{tri}$ (III) with a methanol wash prior to being immunostained (C).
Figure 5:
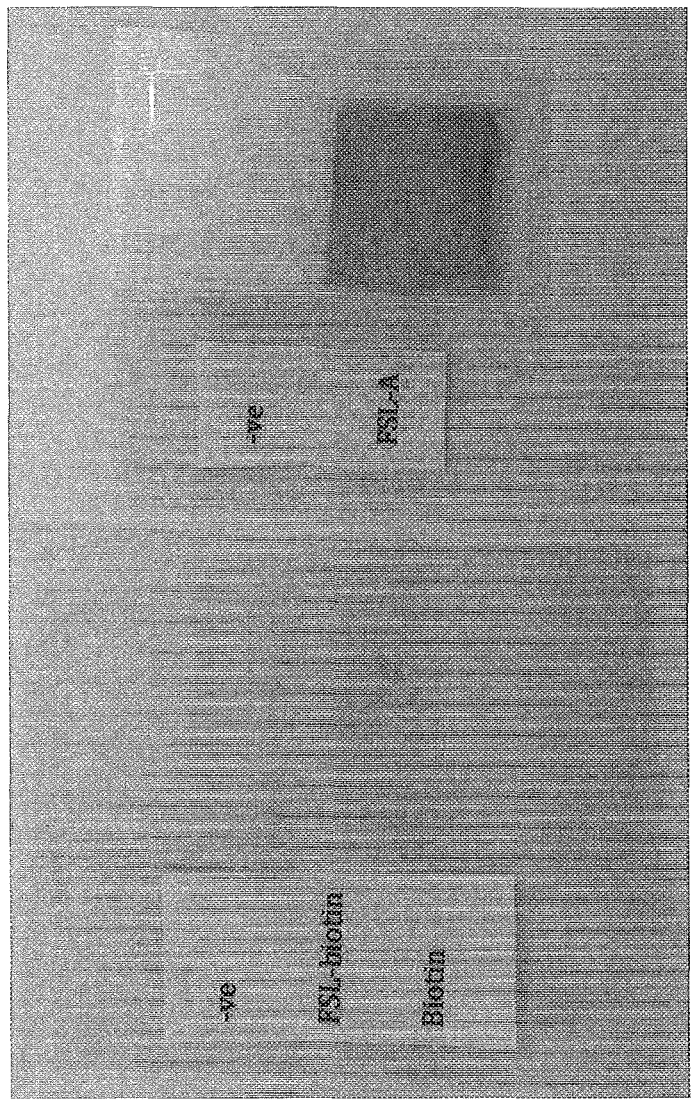
FIG. 5. Photograph of immunostained samples of mats of nanofibres electrospun from a dispersion of PVB alone or in admixture with one of the constructs designated KODE™-biotin (II) ('FSL-biotin'), KODE™-$A_{tri}$ (III) ('FSL-A') or biotin per se. Immunostaining was performed with anti-A antibody.

Samples of functionalized nanofibres were prepared using the apparatus illustrated schematically in FIG. 1. Briefly, a dispersion of polymer is dispensed into an elongated reservoir (1). A star shaped metal wheel (2) rotates in the direction indicated in FIG. 1 and picks up droplets of the dispersion on the points (3) of the wheel (2). A high voltage is maintained between the wheel (2) and the metal collector plate (4) to which a collecting surface such as a cloth or paper backing is affixed. As the wheel (2) rotates the electric field strength overcomes the surface tension of the dispersion and a charged polymer jet is ejected from the pendant droplets carried on the points of the wheel (3) towards the plate (4) causing a mat of fibres (5) of the polymer to be deposited on the backing affixed to the plate (4). Dispersions of PVB when, prepared at a concentration of 10% (w/v) in 100% ethanol. Dispersions of CA were prepared at a concentration of 17% (w/v) in 70:15:15 (v/v/v) MEK/DMA/DMF. Mats of nanofibres electrospun from these dispersions with or without the addition of KODE™ constructs or biotin were used in the following experiments.

Speed of rotation, the distance to the collector plate and voltage were readily adjusted to optimise deposition of the nanofibres electrospun from each of the dispersions. Where KODE™ constructs were added to the dispersions 50 µL of a 10 mg/mL solution of the construct in 100% ethanol was added to a 5 mL volume of the dispersion of the polymer to provide a final concentration of 100 µg/mL. It is anticipated that the deposition of nanofibres can be further optimised by adjustment of the polymer concentration, medium volatility and medium conductivity. Where biotin was added to the dispersions 500 µL of a 250 µg/mL concentration of the solute in 100% ethanol was added to a 5 volume of the dispersions of the polymer to provide a final concentration of 25 µg/mL.

Immunostaining of Electrospun Nanofibres

Mats of nanofibres electrospun from the dispersions were immunostained on their backing papers following blocking of the surface with 2% BSA for 60 minutes. For mats of nanofibres electrospun from dispersions containing the construct designated KODE™-biotin (II) and the respective controls, a 1 µg/mL solution of streptavidin conjugated to alkaline phosphatase (s2890, Sigma) in 2% (w/v) BSA was incubated on the surface at room temperature for 30 minutes. The surface was then washed 6 times in PBS before incubating at room temperature with a 50-fold dilution of NBT/BCIP substrate (11 681 451 001, Roche) in 2:2:1 (mol/mol/mol) Tris-NaCl—MgCl2 buffer (pH 9.5) for, about 2 minutes. The samples were then washed with PBS and air dried.

Figure 6:
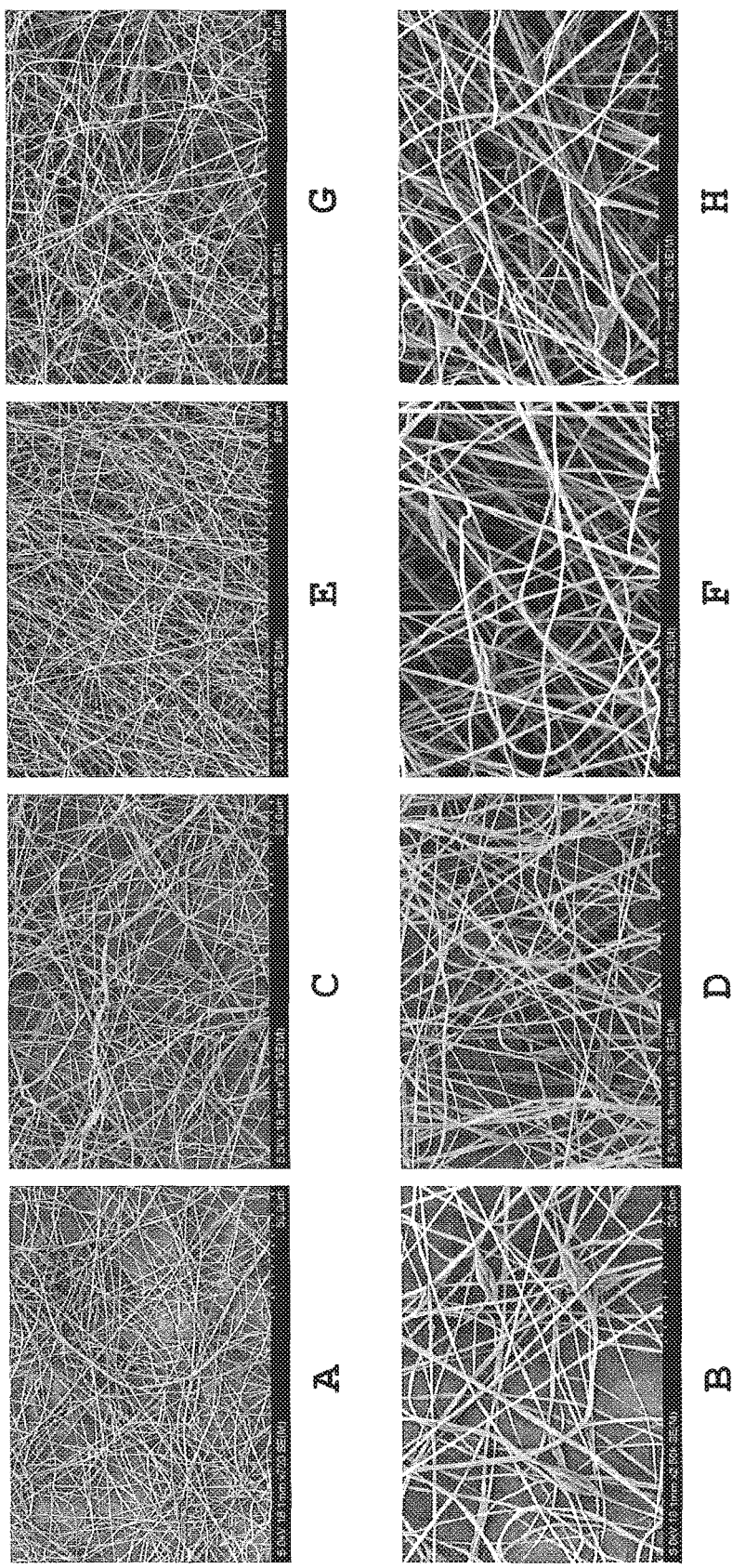
FIG. 6. Scanning electron micrographs of nanofibres electrospun from dispersions of PVB alone (A and B), PVB in admixture with the construct designated KODE™-biotin (II) (C and D), PVB in admixture with the construct designated KODE™-fluorescein (I) (E and F) and PVB in admixture with the construct: designated KODE™-$A_{tri}$ (III) (G and H). Micrographs B, D, F and H are at higher magnification.

For mats of nanofibres electrospun from dispersions containing the KODE™ construct designated KODE™-A (III) and the respective controls, a 5-fold dilution of a mouse anti-A antibody (epiclone, CSL) in 2% BSA was incubated on the surface at room temperature for 30 minutes. The surface was then washed 6 times in PBS before incubating at room temperature with a 1000-fold dilution of alkaline phosphatase conjugated anti-mouse antibody (AQ502A, Millipore) in 2% BSA for 30 minutes. The surface was washed again (6 times, PBS) before incubating with the chromogenic substrate as before. Photomicrographs and photographs of the mats of functionalized nanofibres following immunostaining and their respective controls are provided in FIGS. 2 to 5. Scanning electronmicrographs of the electrospun fibres are provided in FIG. 6.

Printing on Nanofibres

Figure 7:
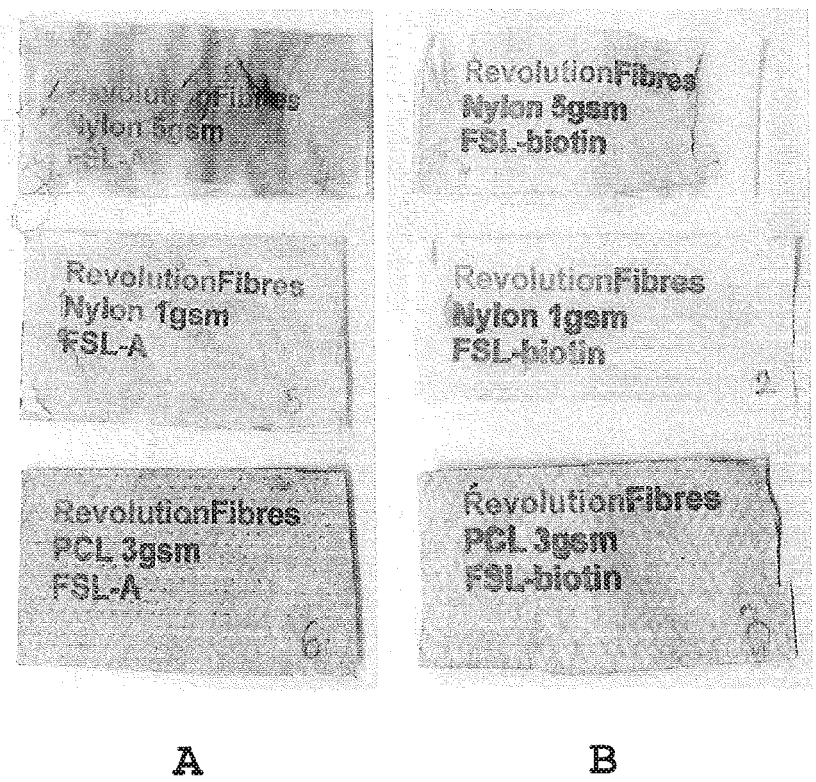
FIG. 7. Immunostaining with alkaline phosphatase conjugated streptavidin of the surface of non-woven mats of nanofibre (5GSM nylon (Upper), 1GSM nylon (middle) and 3GSM PCL (lower)) printed with an aqueous dispersion of either the construct designated KODE™-A$_{tri}$ (III) or the construct designated KODE™-biotin (II) (B). The identity of the substrate and dispersion employed is identified by the words appearing following immunostaining. All substrates sourced from Revolution Fibres (Henderson, Auckland, New Zealand).
Figure 8:
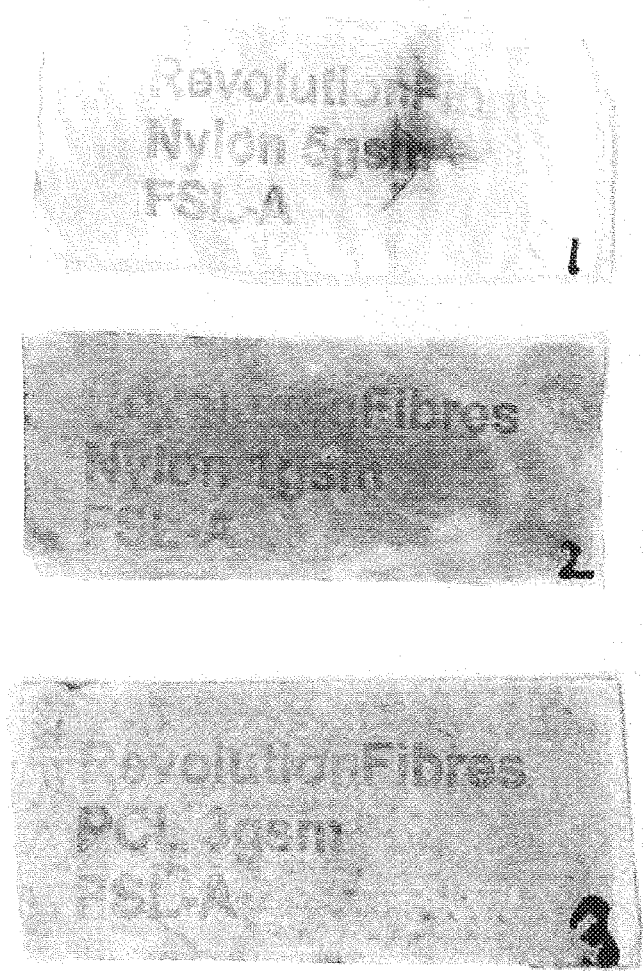
FIG. 8. Immunostaining with alkaline phosphatase conjugated streptavidin of the surface of nanofibre mats (5GSM nylon (Upper), 1GSM nylon (middle) and 3GSM PCL (lower)) printed with a dispersion of the construct designated KODE™-A$_{tri}$ (III) using polyclonal serum.
Figure 9:
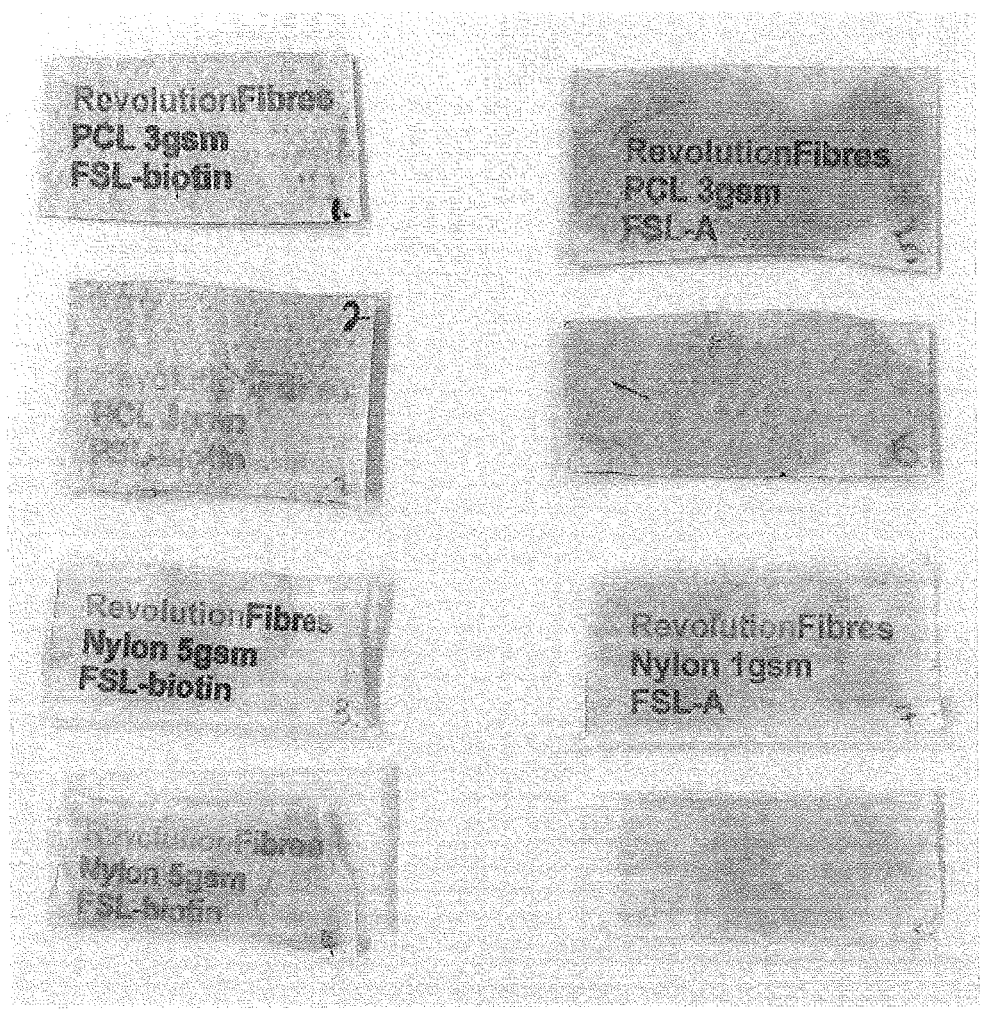
FIG. 9. Immunostaining with alkaline phosphatase conjugated streptavidin of the surface of nanofibre mats (5GSM nylon (Upper), 1GSM nylon (middle) and 3GSM PCL (lower)) both before (first and third rows) and after (second and fourth rows) washing with methanol.

The ability of mats of nanofibres to serve as an improved substrate for the printing of FSL constructs as described in the publication of Bovin et al (2011) was evaluated. Solutions of the construct designated KODE™$A_{tri}$ (III) (FSL-A) and the construct designated KODE™-biotin (II) (FSL-Biotin) were printed on to mats of nanofibres (Revolution Fibres, Henderson, Auckland, New Zealand). An ink jet printer (EPSON STYLUS™ T21) with refillable cartridges modified to hold a smaller volume was employed. The constructs were prepared as solutions and used to fill separate modified cartridges. To facilitate identification and as an illustration of one of the advantages provided by printing FSL constructs the identification of the source of the mats, type of nanofibre and solution were printed. Following printing of the solutions each sample was blocked and immunostained as before. The immunostained samples are presented in FIGS. 7 to 9.

Immobilisation of Cells

Figure 10:
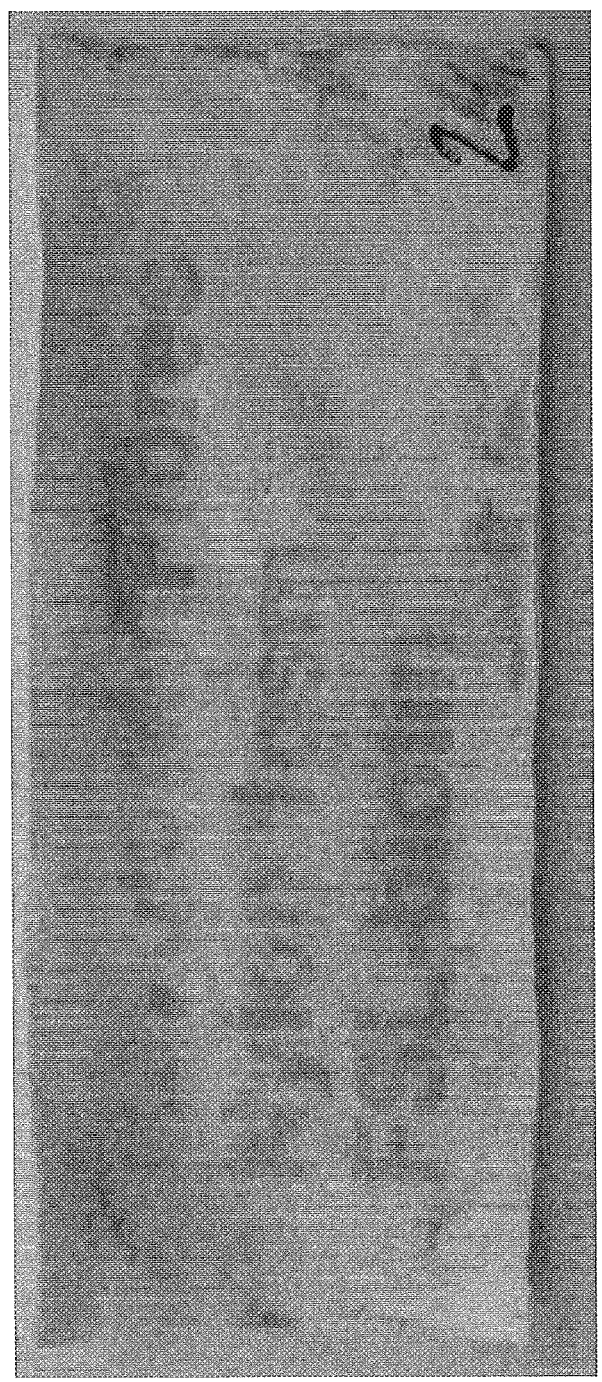
FIG. 10. Photograph of red blood cells modified to incorporate the construct designated KODE™-biotin (II) (kodecytes) attached to avidinylated (streptavidin) substrate following printing with the construct designated KODE™-biotin (II).
Figure 11:
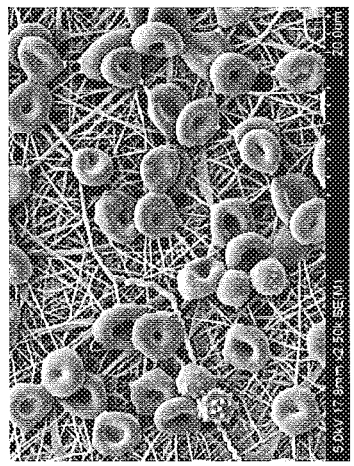
FIG. 11. Scanning electronmicrograph images of red blood cells attached to discrete areas of avidinylated (streptavidin) nanofibre mats following printing with the construct designated KODE™-biotin (II).
Figure 11:
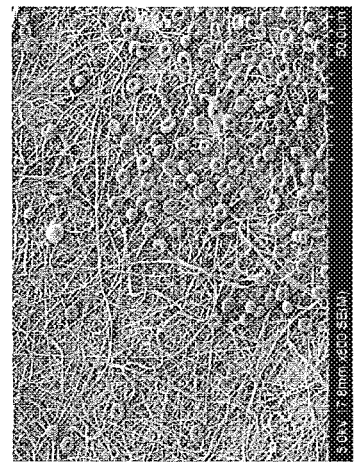
Figure 11:
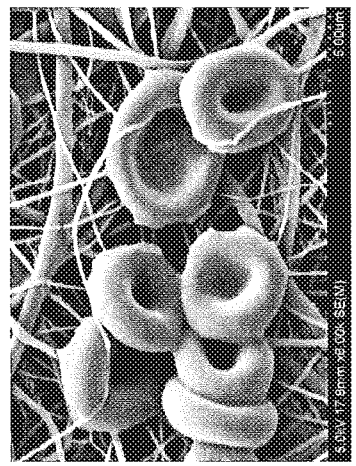
Figure 11:
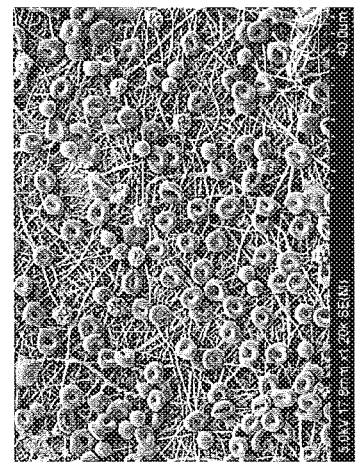
Figure 11:
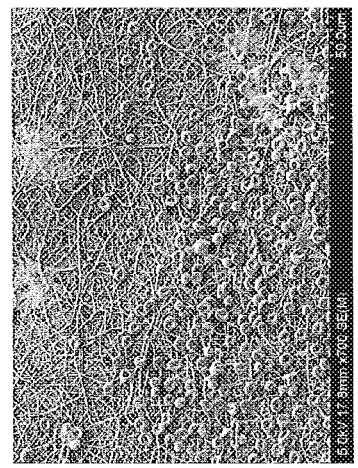

The ability of the printing technique to immobilise red blood cells modified to incorporate the construct designated KODE™-biotin (II) (kodecytes) to discrete areas following avidinylation (streptavidin) of mats of nanofibres also printed with the construct is shown in FIGS. 10 and 11.

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention.

REFERENCED PUBLICATIONS

Bovin et al (2005) Synthetic membrane anchors international application no. PCT/NZ2005/000052 (publ. no. WO 2005/090368 A1)

Bovin et al (2009) Functional lipid constructs international application no. PCT/NZ2008/000266 (publ. no. WO 2009/0483434 A1)

Bovin et al (2011) Printing of constructs international application no. PCT/NZ2010/000127 (publ. no. WO 2011/002310 A1)

Garca et al (2013) Nonwoven membrane as a drug delivery system International application no. PCT/EP2013/056522 (publ. no. NO 2013/144206 A1)

Kiick et al (2006) Multifunctional and biologically active matrices from multicomponent polymeric solutions U.S. patent application Ser. No. 11/395,699 (publ. no. US 2006/0240313 A1)

Korchagina et al (2008) Fluorescent cell markers International application no. PCT/NZ2007/000256 (publ. no. WO 2008/030115 A2)

Seiler et al (2009) Nanofibre matrices formed from electrospun hyperbranched polymers International application no. PCT/EP2009/055045 (publ. no. WO 2009/133059 A2)

Supaphol et al (2012) *Electrospinning of biocompatible polymers and their potentials in biomedical applications* Advances in Polymer Science, 246, 213-239

Tojo et al (2013) Nanofibre U.S. patent application Ser. No. 13/703,315 (publ. no. US 2013/0125912)

Vile et al (2013) Bioactive nanofibres International application no. PCT/IB2012/054626 (publ. no. WO 2013/035072 A1)

The invention claimed is:

1. A functionalized nanofibre comprising an electrospun dispersion of a polymer in admixture with a water-soluble synthetic construct of the structure F-S-L where F is a functional moiety expressed or presented at the surface of the nanofibre, L is a lipid incorporated into the nanofiber and S is a spacer linking F to L via covalent bonds.

2. The functionalized nanofibre of claim 1 where the polymer is cellulose acetate (CA) or poly[(2-propyl-1,3-dioxane-4,6-diyl)methylene](PVB).

3. The functionalized nanofibre of claim 1 where F is a functional moiety selected from the group consisting of: fluorophores of fluorescein, biotin, monosaccharides, disaccharides, trisaccharides and oligosaccharides.

4. The functionalized nanofibre of claim 3 where L is a phosphatidyl-ethanolamine.

5. The functionalized nanofibre of claim 4 where S is selected from the group consisting of:

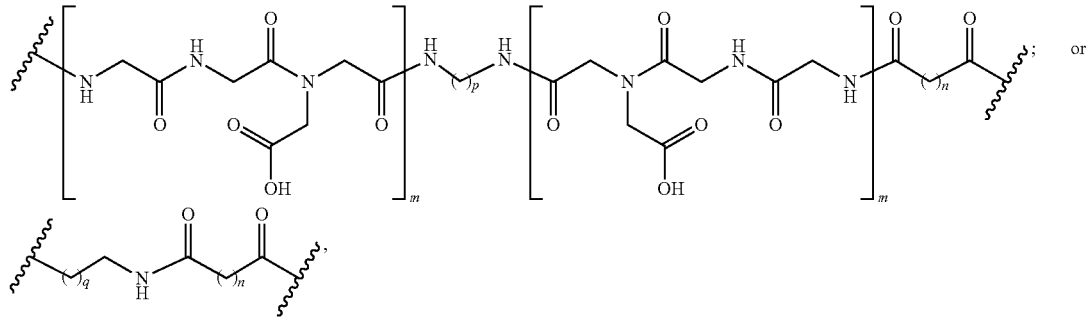

where m is the integer 1, 2 or 4, n is the integer 3, 4 or 5, p is the integer 1, 2 or 3 and q is the integer 2, 3, 4, 5 or 6.

* * * * *